(12) United States Patent
Jensen et al.

(10) Patent No.: US 7,420,068 B2
(45) Date of Patent: *Sep. 2, 2008

(54) CRYSTALLINE COMPOSITION CONTAINING ESCITALOPRAM

(75) Inventors: Kim Bojstrup Jensen, Kobenhavn O (DK); Rikke Eva Humble, Kobenhaven NV (DK); Ken Liljegren, Vaerlose (DK); Troels Volsgaard Christensen, Holbaek (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 552 days.

This patent is subject to a terminal disclaimer.

(21) Appl. No.: 10/948,594

(22) Filed: Sep. 23, 2004

(65) Prior Publication Data
US 2005/0197388 A1 Sep. 8, 2005

Related U.S. Application Data

(62) Division of application No. 10/851,763, filed on May 21, 2004.

(60) Provisional application No. 60/550,909, filed on Mar. 5, 2004.

(51) Int. Cl.
C07D 307/78 (2006.01)
A61K 31/34 (2006.01)

(52) U.S. Cl. ........................ 549/467; 514/469
(58) Field of Classification Search ............... 549/467; 514/469

See application file for complete search history.

(56) References Cited

U.S. PATENT DOCUMENTS

| 4,136,193 A | 1/1979 | Bogeso et al. |
| 4,650,884 A | 3/1987 | Bogeso et al. |
| 4,943,590 A * | 7/1990 | Boegesoe et al. ........... 514/469 |
| RE34,712 E | 8/1994 | Boegesoe et al. |
| 6,566,540 B2 | 5/2003 | Rock et al. |

FOREIGN PATENT DOCUMENTS

| WO | WO-02/087566 A1 | 11/2002 |
| WO | WO-03/000672 A1 | 1/2003 |
| WO | WO-03/006449 A1 | 1/2003 |
| WO | WO-03/011278 A1 | 2/2003 |
| WO | WO-03/051861 A1 | 6/2003 |
| WO | WO2004/014821 | 2/2004 |
| WO | WO2004/085416 | 10/2004 |

OTHER PUBLICATIONS

U.S. Appl. No. 10/851,763 to Jensen et al., filed May 21, 2004.
PCT International Search Report of International Appln. No. PCT/DK2005/000115.

* cited by examiner

*Primary Examiner*—D. Margaret Seaman
*Assistant Examiner*—Nizal S Chandrakumar
(74) *Attorney, Agent, or Firm*—Darby & Darby, P.C.

(57) ABSTRACT

The present invention discloses crystalline particles of escitalopram oxalate which either have a broad particle size distribution or comprise at least 0.01% (w/w) of Z-4-(4-dimethylamino-1-(4-fluorophenyl)-but-1-enyl)-3-hydroxymethyl-benzonitrile, said particles being suitable for use in direct compression.

Furthermore, the invention discloses a novel pharmaceutical unit dosage form containing such crystalline particles of escitalopram oxalate as well as methods for manufacture of such crystalline particles of escitalopram oxalate Finally, the invention provides a method for reduction of the amount of hydroxyl containing impurities in a solution of citalopram or escitalopram.

32 Claims, No Drawings

CRYSTALLINE COMPOSITION CONTAINING ESCITALOPRAM

Under 35 U.S.C. § 119(e), this application claims the benefit of prior U.S. Provisional Application No. 60/550,909, filed Mar. 5, 2004, which is incorporated herein by reference in its entirety.

The present invention relates to crystalline preparations of the oxalate salt of the compound escitalopram (INN-name), which is the S-enantiomer of the well-known antidepressant drug citalopram, i.e. (S)-1-[3-(dimethylamino)propyl]-1-(4-fluorophenyl)-1,3-dihydro-5-isobenzofurancarbonitrile oxalate.

BACKGROUND OF THE INVENTION

Citalopram is a well-known antidepressant drug that has the following structure:

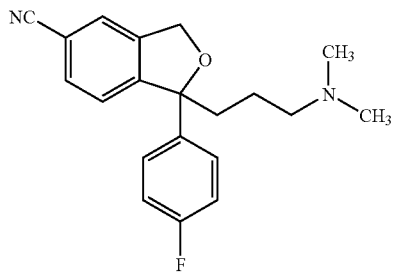

It is a selective, centrally active serotonin (5-hydroxytryptamine; 5-HT) reuptake inhibitor, accordingly having antidepressant activities.

Citalopram was first disclosed in DE 2,657,013, corresponding to U.S. Pat. No. 4,136,193. This patent publication describes the preparation of citalopram by one method and outlines a further method, which may be used for preparing citalopram. The citalopram prepared was isolated in crystalline form as the oxalate, the hydrobromide and the hydrochloride salt, respectively. Furthermore, the citalopram base was obtained as an oil (B.P. 175° C./0.03 mmHg). The publication also outlines the manufacture of tablets containing salts of citalopram. Citalopram is marketed as the hydrobromide and the hydrochloride, respectively.

Escitalopram, the pharmaceutical activity thereof and crystalline escitalopram oxalate are disclosed in U.S. Pat. No 4,943,590. Methods for preparation of pharmaceutical preparations of escitalopram are outlined.

Citalopram is marketed in a number of countries as a tablet prepared by compression of granulated citalopram hydrobromide, lactose and other excipients.

It is well recognised that preparation of tablets with a reproducible composition requires that all the dry ingredients have good flow properties. In cases, where the active ingredient has good flow properties, tablets can be prepared by direct compression of the ingredients. However, in many cases the particle size of the active substance is small, the active substance is cohesive or has poor flow properties.

Further, active substances with a small particle size mixed with excipients having a larger particle size will typically segregate or de-mix during the tabletting process.

The problem of small particle size and poor flowability is conventionally solved by enlarging the particle size of the active substance, usually by granulation of the active ingredient either alone or in combination with a filler and/or other conventional tablet ingredients.

One such granulation method is the "wet" granulation process. Using this method, the dry solids (active ingredients, filler, binder etc.) are blended and moistened with water or another wetting agent (e.g. an alcohol) and agglomerates or granules are built up of the moistened solids. Wet massing is continued until a desired homogenous particle size has been achieved whereupon the granulated product is dried.

An alternative to the "wet" granulation method is the "melt" granulation, which is also known as the "thermal plastic" granulation process, where a low melting solid is used as the granulation agent. Initially, the dry solids are blended and heated until the binder melts. As the binder is liquefied and spreads over the surface of the particles, the particles will adhere to each other and form granules. The binder solidifies upon cooling forming a dry granular product.

Wet granulation as well as melt granulation are energy intensive unit operations requiring complicated and expensive equipment as well as technical skill.

If the active ingredient, however, has suitable flow properties, then the granulation step can be avoided and tablets may be prepared by direct compression which is a cheaper production method.

The process used for the preparation of citalopram hydrobromide results in a product with a very small particle size around 2-20 µm that, as many other particulate products with a small particle size, has very poor flow properties. Thus, in order to achieve appropriate dosing of the citalopram hydrobromide during tabletting, it was considered necessary to make a granulate of citalopram hydrobromide with larger particle size and improved flow properties.

The citalopram tablet that is marketed is a tablet made from granulated citalopram hydrobromide with various excipients.

We have found that escitalopram has significantly different solubility and salt formation properties from the citalopram racemate. For example, the only pharmaceutically crystalline salt known so far is the oxalate, whereas the citalopram racemate forms crystalline hydrobromide and hydrochloride salts as well.

The escitalopram oxalate product prepared by crystallisation from acetone as outlined in U.S. Pat. No 4,943,590 has, as the citalopram hydrobromide product described above, a very small particle size around 2-20 µm resulting in similarly poor flow properties.

WO03/000672 discloses a process for the preparation of racemic as well as enantiomerically pure citalopram from the compound R-4-[4-(dimethylamino)-1-(4'-fluorophenyl)-1-hydroxybutyl]-3-(hydroxymethyl)-benzonitrile by ring-closure under acidic conditions.

WO03/011278 discloses crystalline particles of escitalopram oxalate with a particle size of at least 40 µm. Method for the manufacture of said crystalline particles and pharmaceutical compositions comprising said crystalline particles are also disclosed.

The inventors of the present invention have now surprisingly realised that the particle sizes obtained if escitalopram prepared according to the process disclosed in WO03/000672 is precipitated as the oxalate salt according to the method disclosed in WO03/011278, are significantly smaller than those obtained from prepared by ring-closure of S-4-[4-(dimethylamino)-1-(4'-fluorophenyl)-1-hydroxybutyl]-3-(hydroxy-methyl)-benzonitrile via a labile ester under alkaline conditions.

They have furthermore realised that the reduction in particle size of the escitalopram oxalate crystals is related to the presence of a specific impurity, Z-4-(4-dimethyl-amino-1-(4- fluorophenyl)-but-1-enyl)-3-hydroxymethyl-benzonitrile. This impurity is unique for the acidic ring-closure process as compared to the ring-closure via a labile ester under alkaline conditons.

In view of the fact that direct compression is much simpler and cheaper than the processes involving granulation there is a continued desire for large crystals of escitalopram or pharmaceutical acceptable addition salts thereof.

Laboratory and full-scale research have now resulted in a new and inventive process producing large crystalline particles of escitalopram oxalate, i.e. particles of a size comparable to the size of the filler, by a novel and inventive process for reduction of the amount of Z-4-(4-dimethylamino-1-(4-fluorophenyl)-but-1-enyl)-3-hydroxymethyl-benzonitrile in the solution of escitalopram prior to crystallisation of the oxalate. Said particles are useful for the manufacture of directly compressed tablets. Accurate dosing in capsules may also be with such large particles.

OBJECTS OF THE INVENTION

One aspect of the present invention is to provide crystalline particles of escitalopram oxalate with a broad particle size distribution, said particles being suitable for use in direct compression.

A second aspect of the invention is to provide large crystalline particles of escitalopram oxalate comprising at least 0.01% (w/w) of Z-4-(4-dimethylamino-1-(4-fluorophenyl)-but-1-enyl)-3-hydroxymethyl-benzonitrile, said particles being suitable for use in direct compression.

A third aspect of the invention is to provide a novel pharmaceutical unit dosage form containing crystalline particles of escitalopram oxalate, wherein said particles have a broad particle size distribution and said unit dosage form may be a tablet, which preferably may be prepared by direct compression, or a capsule.

A fourth aspect of the invention is to provide a method for manufacture of large crystalline particles of escitalopram oxalate with a broad particle size distribution.

A fifth aspect of the invention is to provide a method for manufacture of large crystalline particles of escitalopram oxalate comprising reduction of the amount of hydroxyl containing impurities in a solution of escitalopram and crystallising the resulting escitalopram as the oxalate salt.

A sixth aspect of the invention is to provide a method for reduction of the amount of hydroxyl containing impurities in a solution of citalopram or escitalopram.

DETAILED DESCRIPTION OF THE INVENTION

The invention then, inter alia, comprises the following alone or in combination:

Crystalline particles of escitalopram oxalate having a ratio between the median particle size and the particle size at the 95% quantile is less than 0.42, preferably less than 0.40. Such particles are suitable for use in a solid unit dosage form.

Crystalline particles of escitalopram oxalate having a median particle size of at least 40 μm and a content of E- or Z-4-(4-dimethylamino-1-(4-fluorophenyl)-but-1-enyl)-3-hydroxymethyl-benzonitrile of at least 0.01% (w/w), preferably the median particle size of the crystals is in the range of 50-200 μm. Such particles are suitable for use in a solid unit dosage form.

Crystalline particles of escitalopram oxalate having a median particle size of at least 40 μm and being crystallised from a solution wherein the content of E- or Z-4-(4-dimethylamino-1-(4-fluorophenyl)-but-1-enyl)-3-hydroxymethyl-benzonitrile prior to the crystallisation is at least 0.01% (w/w) relative to escitalopram, preferably the median particle size of the crystals is in the range of 50-200 μm. Such particles are suitable for use in a solid unit dosage form.

A solid unit dosage form comprising crystalline particles of escitalopram oxalate wherein said crystalline particles of escitalopram oxalate are according to the invention as described above.

A method for manufacture of crystalline particles of escitalopram oxalate which crystalline particles of escitalopram oxalate are as described above and said method comprises the steps of:

a) Treating a solution comprising escitalopram together with one or more hydroxyl containing impurities with a hydroxyl group scavenger
b) separating the escitalopram from the products resulting from reaction of said hydroxyl containing impurities with said hydroxyl group scavenger
c) optionally transferring the escitalopram into its oxalate salt if the escitalopram is not already in the form of its oxalate salt
d) optionally transferring the escitalopram to a solvent system suitable for the crystallisation process if the escitalopram is not already in such a solvent system
e) gradual cooling of the solution of escitalopram oxalate in said suitable solvent system from a first temperature to a second temperature while maintaining a controlled cooling profile and seeding said solution of escitalopram oxalate by addition of crystals of escitalopram oxalate during said cooling followed by a holding time at said second temperature.

A method for manufacture of crystalline particles of escitalopram oxalate which crystalline particles of escitalopram oxalate are as described above and said method comprises gradual cooling of a solution of escitalopram oxalate in a suitable solvent system from a first temperature to a second temperature while maintaining a controlled cooling profile and seeding said solution of escitalopram oxalate by addition of crystals of escitalopram oxalate during said cooling followed by a holding time at said second temperature wherein said solution of escitalopram comprises at least 0.01% of E- or Z-4-(4-dimethylamino-1-(4-fluorophenyl)-but-1-enyl)-3-hydroxymethyl-benzonitrile.

A method for reducing the amount of hydroxyl containing impurities in citalopram or escitalopram comprising the steps of:

a) Treating a solution comprising citalopram or escitalopram together with one or more such impurities with a hydroxyl group scavenger and
b) separating said citalopram or escitalopram from the products resulting from reaction of said hydroxyl containing impurities with said hydroxyl group scavenger.

The direct compression of escitalopram, a filler and other pharmaceutically acceptable excipients into tablets has the great advantage, that the granulation and a drying step is avoided. Further, as the granulation step is avoided, it is no longer necessary to add a binding agent.

As used herein, "escitalopram oxalate" means any addition salt consisting of escitalopram, oxalic acid and optionally water. Examples of such salts are the hydrogen oxalate salt of escitalopram, i.e. the salt consisting of one molecule of escitalopram per molecule of oxalic acid, as well as the oxalate salt of escitalopram, i.e. the salt consisting of two molecules of escitalopram per molecule of oxalic acid.

As used herein, "crystalline particles" means any combination of single crystals, aggregates and agglomerates.

As used herein, "direct compression" means that the solid unit dosage form is prepared by compression of a simple mixture of the active ingredient and excipients, without the active ingredient having been subjected to an intermediate granulation process in order to embed it in a larger particle and improve its fluidity properties.

As used herein, "binder" means an agent, which is used in wet or melt granulation processes and acts as a binder in the granulated product.

As used herein, "particle size distribution" means the cumulative volume size distribution of equivalent spherical diameters as determined by laser diffraction at 1 bar dispersive pressure in a Sympatec Helos equipment. "Median particle size" "MPS" and X50 refer, correspondingly, each to the median or 50% quantile of said particle size distribution. "X10" and "X95" refer, correspondingly, to the 10% respectively the 95% quantile. "X10/X50" and "X50/X95" refer to the ratio between X10 and X50 respectively X50 and X95.

As used herein, "refluxing temperature" means the temperature at which the solvent or solvent system refluxes or boils at atmospheric pressure.

As used herein, "cooling profile" means the temperature of the crystallisation batch as a function of time.

As used herein, "cooling rate" means the decrease in temperature per time unit.

As used herein, "hydroxyl group scavenger" means a molecule or reactant which is able to react with a hydroxyl group and transform it into another substituent. The hydroxyl group scavenger is preferably selected such that the substituent which the hydroxyl group is transformed into facilitates separation of the transformed molecule or impurity from the escitalopram or citalopram. The hydroxyl group scavenger is preferably selected among those reacting fast with hydroxyl groups under mild conditions without affecting citalopram or escitalopram. Examples of hydroxyl group scavengers are cyclic anhydrides, $POCl_3$, $PCl_5$, $POBr_3$, $PBr_5$, $POI_3$, $PI_5$, $BCl_3$, $BBr_3$ and $BI_3$, which all will introduce an acidic group into the impurity molecule whereupon it may be separated from citalopram and/or escitalopram by extraction into an alkaline aqueous solution from an organic solvent.

Thus in one embodiment of the present invention the crystalline particles of escitalopram oxalate have a median particle size of at least 40 μm, preferably in the range of 50-200 μm.

In one embodiment, the escitalopram oxalate crystals comprise at least 0.01% (w/w) relative to escitalopram of E- or Z-4-(4-dimethylamino-1-(4-fluorophenyl))-but-1-enyl)-3-hydroxymethyl-benzonitrile. In particular embodiments the amount of E- or Z-4-(4-dimethylamino-1-(4-fluorophenyl))-but-1-enyl)-3-hydroxymethyl-benzonitrile in the crystals is in the range of 0.01 to 0.3%, more particularly 0.02 to 0.2%, and most particularly 0.03 to 0.1%.

In a particular embodiment, the hydroxyl containing impurity is Z-4-(4-dimethylamino-1-(4-fluorophenyl))-but-1-enyl)-3-hydroxymethyl-benzonitrile.

In another particular embodiment, the hydroxyl containing impurity is E-4-(4-dimethylamino-1-(4-fluorophenyl))-but-1-enyl)-3-hydroxymethyl-benzonitrile.

Flow, segregation and demixing properties and, hence, the suitability of the escitalopram oxalate crystals for direct compression depend, besides the median particle size, on the particle size distribution, It may for certain purposes such as wet granulation be advantageous to have a broad particle size distribution. Small particles may dissolve during wet granulation and then solidify between the larger crystals upon drying and hence impart strength to the granulate. Further, in certain tabletting processes such as dry granulation (compaction), it may be desirable to have a broader particle size distribution so as to increase the packing efficiency of the particles, and thus the inherent binding capability.

Citalopram, escitalopram or a non-racemic mixture of R- and S-citalopram containing a hydroxyl group containing impurity such as E- or Z-4-(4-dimethylamino-1-(4-fluorophenyl))-but-1-enyl)-3-hydroxymethyl-benzonitrile is dissolved in a suitable solvent such as dry toluene. A hydroxyl group scavenger, such as succinic anhydride in amount sufficient to scavenge the hydroxyl group containing impurity is added to the solution and the mixture is stirred at a suitable temperature, e.g. 45° C., for a suitable period, e.g. 120 minutes.

The impurity is then separated from the citalopram, escitalopram or non-racemic mixture of R- and S-citalopram in a suitable way. Those skilled in the art will know such ways. If the impurity is transformed into an acidic compound, e.g. by reaction with a cyclic anhydride, preferably a cyclic $C_{4-8}$-anhydride, more preferred succinic anhydride, the separation may be done by partitioning between the organic solvent and an alkaline aqueous phase. Water and a base, such as aqueous ammonia are added to a suitable pH, e.g. pH=10.5-11.0. The phases are separated and the organic phase is washed with water. The organic phase is evaporated to yield the citalopram, escitalopram or non-racemic mixture of R- and S-citalopram.

In another aspect of the present invention crystalline particles of escitalopram oxalate having a median particle size of at least 40 μm, preferably in the range of 50-200 μm, and suitable for use in a solid unit dosage form are crystallised from a solution of escitalopram oxalate in a suitable solvent system. Said solvent system may comprise one or more alcohols and optionally water, preferably the solvent system is ethanol. Escitalopram oxalate is preferably dissolved in the solvent system at a temperature in the range between 50° C. and the refluxing temperature of the solvent system, preferably between 60° C. and the refluxing temperature and more preferred between 70° C. and the refluxing temperature, suitably the escitalopram oxalate is dissolved at the refluxing temperature. The amounts of pharmaceutically acceptable salt of escitalopram and solvent used are preferably corresponding to a solvent:solute weight ratio in the range of 0.05:1 to 0.6:1, more preferred 0.1:1 to 0.5:1 and most preferred 0.2:1 to 0.4:1. The solution of escitalopram oxalate is gradually cooled down to the temperature, at which the crystals will be isolated from the mother liquor, in the range of 0-20° C., preferably 0-15° C., and more preferred 7-15° C. maintaining a controlled cooling profile so that the cooling rate in an initial cooling period does not exceed 0.6° C./min, and preferably the cooling rate is kept within the range of 0.2-0.4° C./min, and said initial cooling period extends until the temperature of the crystallisation batch is below 60° C., preferably below 50° C. and more preferred below 40° C., suitably the cooling rate may be kept in this range for the entire cooling. The crystallisation batch is seeded by addition of crystals of escitalopram oxalate at least once during the cooling time in order to avoid excessive supersaturation with respect to escitalopram oxalate and resulting spontaneous crystallisation into small crystalline particles. The seeding is preferably repeated in order to ensure constant presence of crystalline escitalopram oxalate during the cooling, suitably the crystallisation batch is seeded semicontinuosly until crystallisation has started. The crystallisation batch is optionally kept at said second temperature for a holding time during which there may occur crystal growth. In a particular embodiment said holding time is at least 1 hour, preferably in the range of 4 to 24 hours and more preferred 6 to 12 hours.

Finally, the crystalline particles of escitalopram oxalate are isolated from the mother liquor using conventional separation techniques, e.g. filtration.

In a particular embodiment, the solution from which the escitalopram oxalate is crystallised, comprises at least 0.01% of E- or Z-4-(4-dimethylamino-1-(4-fluorophenyl)-but-1-enyl)-3-hydroxymethyl-benzonitrile. In particular embodiments the amount of E- or Z-4-(4-dimethylamino-1-(4-fluorophenyl)-but-1-enyl)-3-hydroxymethyl-benzonitrile in the crystals is in the range of 0.01 to 0.5%, more particularly 0.01 to 0.3%, even more particularly 0.02 to 0.2%, and most particularly 0.03 to 0.1%.

In a particular embodiment, the hydroxyl containing impurity is Z-4-(4-dimethylamino-1-(4-fluorophenyl)-but-1-enyl)-3-hydroxymethyl-benzonitrile.

In another particular embodiment, the hydroxyl containing impurity is E-4-(4-dimethylamino-1-(4-fluorophenyl)-but-1-enyl)-3-hydroxymethyl-benzonitrile.

The escitalopram, which is to be crystallised as escitalopram oxalate, is in another particular embodiment the product of a method of manufacture comprising the method described above for reduction of the content hydroxyl group containing impurities by reaction with a hydroxyl group scavenger.

The methods described above for reduction of the amount of hydroxyl group containing impurities and crystallisation may be combined with each other and/or with the process for the preparation of racemic citalopram and/or S- or R-citalopram by separation of a mixture of R- and S-citalopram with more than 50% of one of the enantiomers into; a fraction of racemic citalopram and/or a fraction of S-citalopram or R-citalopram containing low amounts of the other enantiomer as disclosed in WO03/000672 which is hereby included by reference.

Such combinations include but are not limited to: hydroxyl scavenging followed by crystallisation of escitalopram oxalate; hydroxyl scavenging by separation of racemic citalopram and escitalopram followed by crystallisation of escitalopram oxalate; separation of racemic citalopram and escitalopram followed by hydroxyl scavenging followed by crystallisation of escitalopram oxalate; and separation of racemic citalopram and escitalopram followed by crystallisation of escitalopram oxalate.

In one embodiment of the invention, the present invention relates to a tablet prepared from a mixture of crystalline particles of escitalopram oxalate and pharmaceutically acceptable excipients wherein said crystalline particles of escitalopram oxalate are according to the invention as described above. Such tablets may be made by one of the following tabletting methods: Direct compression, dry granulation (compaction), wet granulation or melt granulation. In a particular embodiment, the tablet is prepared by direct compression. In another particular embodiment, the tablet is prepared by dry granulation (compaction). In yet another particular embodiment, the tablet is prepared by wet granulation. In yet another particular embodiment, the tablet is prepared by melt granulation.

In another embodiment, the present invention relates to a solid unit dosage form prepared by filling a mixture of crystalline particles of escitalopram oxalate and pharmaceutically acceptable excipients into a capsule wherein said crystalline particles of escitalopram oxalate are according to the invention as described above, preferably the capsule is a hard gelatine capsule.

Preferably, the solid unit dosage forms according to the invention do not contain a binder.

The solid unit dosage form according to the invention may contain 1-60% w/w active ingredient calculated as escitalopram base, particularly 4-40% w/w active ingredient calculated as escitalopram base, evenly particularly 1-30% w/w active ingredient calculated as escitalopram base, more particularly 4-20% w/w active ingredient calculated as escitalopram base and most pre particularly 6-10% w/w active ingredient calculated as escitalopram base. Suitably, the solid unit dosage form of the invention contains 8% w/w active ingredient calculated as escitalopram base.

The solid unit dosage form according to the invention may contain a filler selected from lactose, or other sugars e.g. sorbitol, mannitol, dextrose and sucrose, calcium phosphates (dibasic, tribasic, hydrous and anhydrous), starch, modified starches, microcrystalline cellulose, calcium sulphate and/or calcium carbonate. In a preferred embodiment, the solid unit dosage form of the invention does not contain lactose.

Suitably the filler is a microcrystalline cellulose such as ProSolv SMCC90 manufactured by Penwest Pharmaceuticals or Avicel PH 200 manufactured by FMC Corporation.

Besides the active ingredient and filler, the solid pharmaceutical unit dosage forms may include various other conventional excipients such as disintegrants and optionally minor amounts of lubricants, colorants and sweeteners.

Lubricants used according to the invention may suitably be one or more selected from the group comprising metallic stearates (magnesium, calcium, sodium), stearic acid, wax, hydrogenated vegetable oil, talc and colloidal silica.

Preferably the lubricant is one or more selected from the group comprising talc, magnesium stearate or calcium stearate. Suitably the lubricant is a combination of talc and magnesium stearate. The weight percent of magnesium stearate in the solid unit dosage form is preferably in the range of 0.4% to 2%, and more preferred in the range of 0.7% to 1.4%.

Disintegrants include sodium starch glycolate, croscarmellose, crospovidone, low substituted hydroxypropylcellulose, modified cornstarch, pregelatizined starch and natural starch. Suitably the disintegrant is crosscarmellose such Ac-Di-Sol manufactured by FMC.

Optionally the solid, pharmaceutical unit dosage form of the invention may be coated. Suitably the coating is a film coating based on conventional coating mixtures such as Opadry OY-S-28849, white manufactured by Colorcon.

The solid, pharmaceutical unit dosage form of the invention may be prepared by conventional methods using a tablet press with forced feed capability.

The filled, hard gelatine capsule of the invention may be prepared by conventional methods using a capsule filler suitable for powder filling.

EXAMPLES

In the following, the invention is illustrated by way of examples. However, the examples are merely intended to illustrate the invention and should not be construed as limiting.

Example 1

Scavenging of Hydroxyl Containing Impurity by Succinic Anhydride

A mixture of R- and S-Citalopram (55.5 g) containing 0.6% of Z-4-(4-dimethylamino-1-(4-fluorophenyl)-but-1-enyl)-3-hydroxymethyl-benzonitrile is dissolved in dry toluene (145.0 g). Succinic anhydride (0.5 g) is added to the solution and the mixture is stirred at 45° C. (120 minutes). Water (230 ml) and aqueous ammonia (25% by weight) (3 ml) is added (pH=10.5-11.0). The phases are separated and the toluene phase is washed with water (3×120 ml). The toluene phase is evaporated and the yield is 53.0 g (95%). The product contains 0.06% of Z-4-(4-dimethylamino-1-(4-fluorophenyl)-but-1-enyl)-3-hydroxymethyl-benzonitrile.

Example 2

Production Scale Crystallisation of Escitalopram Oxalate

A large number of batches of crude escitalopram oxalate have been recrystallised in production scale according to the procedure described below. The batches comprises:
a) Escitalopram prepared by acidic ring-closure of the R-form of the diol precursor as described in WO03/000672 followed by scavenging of hydroxyl containing impurity by a production scale version of the process described in example 1 followed by separation of racemic citalopram and escitalopram as described in WO03/000672. These batches contain Z-4-(4-dimethylamino-1-(4-fluorophenyl)-but-1-enyl)-3-hydroxymethyl-benzonitrile, typically in the range of 0.05% (w/w) relative to escitalopram. These batches are referred to as R-diol batches.
b) Escitalopram prepared by ring-closure of the S-form of the diol precursor via an activated ester under alkaline conditions as described in U.S. Pat. No. 4,943,590. These batches do not contain Z-4-(4-dimethylamino-1-(4-fluorophenyl)-but-1-enyl)-3-hydroxymethyl-benzonitrile. These batches are referred to as S-diol batches.

Production Procedure 100 kg to 300 kg of crude escitalopram oxalate is charged to a first reactor, R1. 4.1-4.3 L ethanol per kg crude escitalopram oxalate is charged to R1. The solution is mixed and heated to the boiling point (~80° C.). When every thing is dissolved the solution is transferred through a filter to a second reactor, R2.

The agitator on R2 is started (40-60 rpm) and the solution is heated to the boiling point once again. When everything is dissolved in R2, the automatic cooling is started and the solution is cooled gradually according to the cooling rates in table 1.

TABLE 1

Cooling rates for automatic cooling during recrystallisation of escitalopram oxalate

| Interval [° C.] | Rate [° C./min] |
| --- | --- |
| Above 70.0 | 0.151 |
| 70.0-66.0 | 0.250 |
| 66.0-60.0 | 0.300 |
| 60.0-56.4 | 0.327 |
| 56.4-52.0 | 0.400 |
| 52.0-47.6 | 0.550 |
| 47.6-35.0 | 0.700 |
| 35.0-10.0 | 0.830 |

The solution is seeded with 0.02-0.04 kg escitalopram oxalate for every 3° C. the temperature is decreased until crystallization is noticed. The solution is automatically cooled until 15° C.

The suspension is pumped to the filter dryer, where it is washed and dried. If the suspension is not transferred immediately the temperature must be kept at 0-15° C. The filter cake is dried by vacuum. When the cake is dry, it is washed with 1.1-1.2 L ethanol per kg crude escitalopram oxalate charged. The cake is dried once again and the cake is heated for final drying in approximately 12 hours. Temperature=50-60° C., pressure<0.13 Bar (abs.).

The filter dryer is emptied and the escitalopram oxalate is sent to deagglomeration, for deagglomeration of agglomerates formed during drying of the crystals. The dried escitalopram oxalate is milled to separate the crystals from each other. During the milling the size and shape of the individual crystals is not changed.

The resulting escitalopram oxalate batches had particle characteristics as shown in table 2.

TABLE 2

Particle characteristics for escitalopram oxalate crystals.

| | S-diol batches | | | R-diol batches | | |
| --- | --- | --- | --- | --- | --- | --- |
| Batch | X50 | X10/X50 | X50/X95 | Batch | X50 | X10/X50 | X50/X95 |
| 1 | 171 | 0.13 | 0.44 | 47 | 93 | 0.12 | 0.33 |
| 2 | 153 | 0.07 | 0.43 | 48 | 91 | 0.11 | 0.33 |
| 3 | 158 | 0.09 | 0.43 | 49 | 74 | 0.11 | 0.26 |
| 4 | 171 | 0.15 | 0.44 | 50 | 116 | 0.14 | 0.39 |
| 5 | 166 | 0.10 | 0.47 | 51 | 74 | 0.09 | 0.29 |
| 6 | 165 | 0.13 | 0.46 | 52 | 93 | 0.11 | 0.38 |
| 7 | 163 | 0.10 | 0.47 | 53 | 92 | 0.17 | 0.38 |
| 8 | 171 | 0.15 | 0.44 | 54 | 90 | 0.20 | 0.37 |
| 9 | 171 | 0.15 | 0.47 | 55 | 108 | 0.09 | 0.39 |
| 10 | 166 | 0.11 | 0.47 | 56 | 100 | 0.09 | 0.39 |
| 11 | 174 | 0.11 | 0.46 | 57 | 98 | 0.08 | 0.36 |
| 12 | 162 | 0.07 | 0.44 | 58 | 102 | 0.09 | 0.33 |
| 13 | 180 | 0.11 | 0.46 | 59 | 76 | 0.11 | 0.30 |
| 14 | 165 | 0.11 | 0.44 | 60 | 92 | 0.10 | 0.36 |
| 15 | 178 | 0.13 | 0.48 | 61 | 96 | 0.08 | 0.35 |
| 16 | 162 | 0.12 | 0.47 | | | | |
| 17 | 138 | 0.14 | 0.43 | | | | |
| 18 | 168 | 0.11 | 0.44 | | | | |
| 19 | 166 | 0.11 | 0.46 | | | | |
| 20 | 160 | 0.12 | 0.44 | | | | |
| 21 | 121 | 0.07 | 0.36 | | | | |
| 22 | 141 | 0.08 | 0.41 | | | | |
| 23 | 166 | 0.08 | 0.43 | | | | |
| 24 | 126 | 0.08 | 0.42 | | | | |
| 25 | 123 | 0.09 | 0.42 | | | | |
| 26 | 159 | 0.11 | 0.44 | | | | |
| 27 | 156 | 0.12 | 0.46 | | | | |
| 28 | 147 | 0.12 | 0.46 | | | | |
| 29 | 169 | 0.12 | 0.47 | | | | |
| 30 | 181 | 0.08 | 0.44 | | | | |
| 31 | 147 | 0.07 | 0.39 | | | | |
| 32 | 184 | 0.09 | 0.45 | | | | |
| 33 | 173 | 0.10 | 0.43 | | | | |
| 34 | 161 | 0.09 | 0.42 | | | | |
| 35 | 171 | 0.11 | 0.44 | | | | |
| 36 | 159 | 0.12 | 0.43 | | | | |
| 37 | 160 | 0.13 | 0.45 | | | | |
| 38 | 157 | 0.11 | 0.45 | | | | |
| 39 | 153 | 0.08 | 0.44 | | | | |
| 40 | 163 | 0.10 | 0.44 | | | | |
| 41 | 157 | 0.11 | 0.45 | | | | |
| 42 | 156 | 0.12 | 0.45 | | | | |
| 43 | 129 | 0.10 | 0.40 | | | | |
| 44 | 139 | 0.12 | 0.40 | | | | |
| 45 | 150 | 0.12 | 0.42 | | | | |
| 46 | 195 | 0.09 | 0.46 | | | | |

Comparative Example 1

A wet filter cake obtained by precipitation of crude escitalopram oxalate by mixing of ethanolic solutions of escitalopram prepared by ring-closure via a labile ester under alkaline conditions and oxalic acid, respectively, and containing approximately 35 kg escitalopram oxalate was suspended in 322 L ethanol. The material was dissolved by heating to reflux, and 150 L ethanol was removed by distillation. Cooling was applied, and the mixture was cooled from reflux to 15° C. with a cooling rate between 0.2 and 0.5° C./min in the temperature interval 80 to 40° C. During cooling, the mixture was seeded with escitalopram oxalate at 75, 65 and 60° C. (10 g each time). The crystallisation mixture was kept at 15° C. for 10 hours before the crystalline escitalopram oxalate was isolated. Purified escitalopram oxalate (27.7 kg, 58.2% of theory) was obtained by filtration of the crystallisation mixture, washing with ethanol and drying of the filter cake. Particle size distribution for the resulting escitalopram oxalate is listed in table 3.

TABLE 3

Particle size distribution (Sympatec Helos) for escitalopram oxalate crystals and ProSolv SMCC90

| Quantile (%) | Example 1 (μm) | ProSolv SMCC90 (μm) |
| --- | --- | --- |
| 90 | 455 | 291 |
| 50 | 163 | 130 |
| 10 | 13 | 37 |

Comparative Example 2

Tablet prepared by direct compression of large crystalline particles of escitalopram oxalate.

Tablet Ingredients

| Tablet core | | |
| --- | --- | --- |
| Escitalopram oxalate | 2554 g | (10.2% w/w) |
| Talc | 1400 g | (5.6% w/w) |
| ProSolv SMCC90 | 19896 g | (79.6% w/w) |
| Ac-Di-Sol | 900 g | (3.6% |
| Magnesium stearate | 250 g | (1.0% w/w) |

| Film coating | | |
| --- | --- | --- |
| Opadry OY-S-28849, white | 625 g | (2.5% w/w of core weight) |

Crystalline particles of escitalopram oxalate from example 1 and talc were sieved through 710 μm screen and blended at 6 rpm for 15 min in a 100 liter Bohle PTM 200 mixer. ProSolv SMCC90 and Ac-Di-Sol were added and blending continued for 15 min. Magnesium stearate was sieved through 710 μm screen and added and blending continued for 3 min.

25 kg of the resulting mixture was tabletted (125.000 tablets/hour) on a Korsch PH 230 tablet press fitted with oblong, embossed, scored 5.5×8 mm punches. Tablet core weight was set to 125 mg. The nominal yield was 200.000 tablets. The tablet press was run until the mixture level was just above the forced feeder, i.e. the tabletting was continued as long as possible in order to identify possible segregation tendencies in the last quantities of mixture. The tablets produced had satisfactory technical properties.

Those skilled in the art will easily realise that crystals according to the invention can be used in the manufacture of tablets in similar ways.

The invention claimed is:

1. A method for the manufacture of crystalline particles of escitalopram oxalate, wherein the ratio between the median particle size and the particle size at the 95% quantile is less than 0.42, comprising the steps of:
   a) treating a solution comprising escitalopram together with one or more hydroxyl containing impurities with a hydroxyl group scavenger;
   b) separating the escitalopram from the products resulting from reaction of said hydroxyl containing impurities with said hydroxyl group scavenger;
   c) optionally transferring the escitalopram into its oxalate salt if the escitalopram is not already in the form of its oxalate salt;
   d) optionally transferring the escitalopram to a solvent system suitable for the crystallisation process if the escitalopram is not already in such a solvent system; and
   e) gradually cooling the solution of escitalopram oxalate in said suitable solvent system from a first temperature to a second temperature while maintaining a controlled cooling profile and seeding said solution of escitalopram oxalate by addition of crystals of escitalopram oxalate during said cooling.

2. The method according to claim 1, wherein the solution of escitalopram oxalate of step (e) comprises at least 0.01% of E- or Z-4-(4-dimethylamino-1-(4-fluorophenyl)-but-1-enyl)-3-hydroxymethyl-benzonitrile.

3. The method according to claim 2, wherein said solvent system comprises one or more alcohols and optionally water.

4. The method according to claim 3, wherein the solvent system is ethanol.

5. The method according to claim 2, wherein the solute:solvent weight ratio is in the range of 0.05:1 to 0.6:1.

6. The method according to claim 5, wherein the solute:solvent weight ratio is in the range of 0.1:1 to 0.5:1.

7. The method according to claim 6, wherein the solute:solvent weight ratio is in the range of 0.2:1 to 0.4:1.

8. The method according to claim 2, wherein said first temperature is in the range between 50° C. and the refluxing temperature of the solvent system.

9. The method according to claim 8, wherein said first temperature is in the range between 60° C. and the refluxing temperature.

10. The method according to claim 9, wherein said first temperature is in the range between 70° C. and the refluxing temperature.

11. The method according to claim 2, wherein said second temperature is in the range of 0-20° C.

12. The method according to claim 11, wherein said second temperature is in the range of 0-15° C.

13. The method according to claim 12, wherein said second temperature is in the range of 7-15° C.

14. The method according to claim 2, wherein said controlled cooling profile comprises an initial cooling period where the cooling rate is kept within a fixed range.

15. The method according to claim 14, wherein said initial cooling period covers the period until the temperature is below 60° C.

16. The method according to claim 15, wherein said initial cooling period covers the period until the temperature is below 50° C.

17. The method according to claim 16, wherein said initial cooling period covers the period until the temperature is below 40° C.

18. The method according to claim 14, wherein said cooling rate is kept within the range of 0-0.6° C./min.

19. The method according to claim 18, wherein said cooling rate is kept within the range of 0.2-0.4° C./min.

20. The method according to claim 2, wherein said seeding is done two or more times during the initial cooling.

21. The method according to claim 2, wherein, the crystalline particles after said holding time are isolated from the mother liquor by conventional solid/liquid separation techniques.

22. The method according to claim 21, wherein, the crystalline particles after said holding time are isolated from the mother liquor by filtration.

23. The method according to claim 2, wherein the hydroxyl group scavenger is selected from cyclic anhydrides.

24. The method according to claim 23, wherein the hydroxyl group scavenger is a cyclic $C_{4-8}$-anhydride.

25. The method according to claim 24, wherein the hydroxyl group scavenger is succinic anhydride.

26. The method according to claim 23, wherein the separation of citalopram or escitalopram from the products resulting from reaction of the hydroxyl containing impurities with said hydroxyl group scavenger is performed by extraction of said products resulting from reaction of said hydroxyl containing impurities with said hydroxyl group scavenger into an alkaline aqueous solution from a solution of said citalopram or escitalopram in an organic solvent.

27. A method for the manufacture of crystalline particles of escitalopram oxalate, wherein the ratio between the median particle size and the particle size at the 95% quantile is less than 0.42, comprising:
   gradual cooling of a solution of escitalopram oxalate in a suitable solvent system from a first temperature to a second temperature while maintaining a controlled cooling profile and seeding said solution of escitalopram oxalate by addition of crystals of escitalopram oxalate during said cooling wherein said solution of escitalopram oxalate comprises at least 0.01% of E- or Z-4-(4-dimethylamino-1-(4-fluorophenyl)-but-1-enyl)-3-hydroxymethyl-benzonitrile.

28. A method for reducing the amount of hydroxyl containing impurities in citalopram or escitalopram, comprising the steps of:
   a) treating a solution comprising citalopram or escitalopram together with one or more hydroxyl containing impurities with a hydroxyl group scavenger; and
   b) separating said citalopram or escitalopram from the products resulting from reaction of hydroxyl containing impurities with said hydroxyl group scavenger.

29. The method according to claim 28, wherein the hydroxyl group scavenger is selected from cyclic anhydrides.

30. The method according to claim 29, wherein the hydroxyl group scavenger is a cyclic $C_{4-8}$-anhydride.

31. The method according to claim 30, wherein the hydroxyl group scavenger is succinic anhydride.

32. The method according to claim 29, wherein the separation of citalopram or escitalopram from the products resulting from reaction of the hydroxyl containing impurities with said hydroxyl group scavenger is performed by extraction of said products resulting from reaction of said hydroxyl containing impurities with said hydroxyl group scavenger into an alkaline aqueous solution from a solution of said citalopram or escitalopram in an organic solvent.

* * * * *